US005792865A

United States Patent [19]
Flood et al.

[11] Patent Number: 5,792,865
[45] Date of Patent: Aug. 11, 1998

[54] CARBOXYLATED AMINO-1,3,5-TRIAZINES, DERIVATIVES THEREOF AND PROCESSES FOR PREPARING THE SAME

[75] Inventors: Lawrence Allen Flood, Norwalk, Conn.; Ram Baboo Gupta, Bronx, N.Y.

[73] Assignee: Cytec Technology Corp., Stamford, Conn.

[21] Appl. No.: 444,000

[22] Filed: May 18, 1995

Related U.S. Application Data

[62] Division of Ser. No. 286,835, Aug. 5, 1994.

[51] Int. Cl.$^6$ .......... C07D 251/40; C07D 241/42; C07D 251/48; C07D 251/54
[52] U.S. Cl. .......... 544/194; 544/198; 544/200; 544/205; 544/206; 544/207
[58] Field of Search .......... 544/194, 198, 544/200, 205, 206, 207

[56] References Cited

U.S. PATENT DOCUMENTS

| | | | |
|---|---|---|---|
| 4,102,801 | 7/1978 | Brodoway | 252/182 |
| 4,192,815 | 3/1980 | Sheludyakov et al. | 260/453 |
| 4,400,526 | 8/1983 | Kanner et al. | 556/420 |
| 4,467,089 | 8/1984 | Bechara | 544/351 |
| 4,939,213 | 7/1990 | Jacobs, III et al. | 525/329.9 |
| 5,055,577 | 10/1991 | Riley et al. | 544/172 |
| 5,084,541 | 1/1992 | Jacobs, III et al. | 528/45 |
| 5,189,205 | 2/1993 | McGhee et al. | 560/345 |
| 5,200,547 | 4/1993 | Riley et al. | 558/265 |
| 5,223,638 | 6/1993 | McGhee et al. | 560/24 |
| 5,288,865 | 2/1994 | Gupta | 544/200 |
| 5,641,885 | 6/1997 | Flood et al. | 544/194 |

FOREIGN PATENT DOCUMENTS

| | | |
|---|---|---|
| 0511948A2 | 11/1992 | European Pat. Off. |
| 0556538A1 | 8/1993 | European Pat. Off. |
| 0628542A1 | 12/1994 | European Pat. Off. |
| WO94/08951 | 4/1994 | WIPO |
| WO94/08952 | 4/1994 | WIPO |
| WO94/08953 | 4/1994 | WIPO |
| WO94/17032 | 8/1994 | WIPO |

OTHER PUBLICATIONS

Yoshida and Inoue, "A New Synthesis of Carbamic Esters from Carbon Dioxide, Epoxides, and Amines," *J.C.S. Perkin I*, 3146–50 (1979).

Tsuda et al., "Preparation of Urethanes from Carbon Dioxide via a Copper(I) Carbamato–complex," *J.C.S. Chem. Comm.*, 815–16 (1978).

Yoshida et al., "A Direct Synthesis of Carbamate Ester from Carbon Dioxide, Amine and Alkyl Halide," *Chemistry Letters*, 1571–72 (1984).

Yoshida et al., "Novel Synthesis of Arylcarbamic Esters from Carbon Dioxide and Aromatic Amine via a Zinc Carbamate," *Bull. Chem. Soc. Jpn.*, 61, 2913–16 (1988).

Yoshida et al., "Novel Synthesis of Carbamate Esters from Carbon Dioxide, Amines, and Alkyl Halides," *Bull. Chem. Soc. Jpn.*, 62, 1534–38 (1989).

Yamzaki et al., "Polycarbonate, –Urethane and –Urea from Carbon Dioxide and Carbonates," *Polymer Preprints, National ACS Meeting*, 146–49 (Honoluly, Hawaii 1979).

Aresta and Quaranta, "Role of the Macrocyclic Polyether in the Synthesis of N–Alkylcarbamate Estes from Primary Amines, $CO_2$ and Alkyl Halides in the Presence of Crown–Ethers," *Tetrahedron*, 48(8), 1515–30 (1992).

McGhee et al., "Highly Selective Generation of Urethanes from Amines, Carbon Dioxide and Alkyl Chlorides," *J. Chem. Soc., Chem. Commun.*, 669–700 (1994).

Smolin and Rapoport, *s–Triazines and Derivatives*, Interscience Publishers Inc., New York. pp. 333–338 and 385–386 (1959).

*The Chemistry of Melamine*, American Cyanamid Company, pp. 3–51 (1954).

*Primary Examiner*—Vogendra N. Gupta
*Attorney, Agent, or Firm*—Pennie & Edmonds

[57] ABSTRACT

The present invention relates generally to carboxylated amino-1,3,5-triazines and the preparation thereof via carboxylation of amino-1,3,5-triazines with carbon dioxide and a base. These carboxylated amino-1,3,5-triazines find use, for example, as intermediates in the production of other useful amino-1,3,5-triazine derivatives, and particularly carbamate and isocyanate functional 1,3,5-triazines. The present invention also relates to the preparation of such carbamate and isocyanate functional 1,3,5-triazines.

23 Claims, No Drawings

CARBOXYLATED AMINO-1,3,5-TRIAZINES, DERIVATIVES THEREOF AND PROCESSES FOR PREPARING THE SAME

This application is a Divisional application under 37 CFR 1.60, of pending application Ser. No. 08/286,835 filed on Aug. 5, 1994.

BACKGROUND OF THE INVENTION

1. Field of the Invention

The present invention relates generally to carboxylated amino-1,3,5-triazines and the preparation thereof via carboxylation of amino-1,3,5-triazines with carbon dioxide and a base. These carboxylated amino-1,3,5-triazines find use, for example, as intermediates in the production of other useful amino-1,3,5-triazine derivatives, and particularly carbamate and isocyanate functional 1,3,5-triazines. The present invention also relates to the preparation of such carbamate and isocyanate functional 1,3,5-triazines.

2. Description of Related Art

Various derivatives of amino-1,3,5-triazines are described in the literature as being utilized in a wide variety of fields. An important use of certain of these derivatives, such as the alkoxymethyl derivatives of melamine and guanamines, is as crosslinkers and/or reactive modifiers in curable compositions which contain resins having active hydrogen groups. While alkoxymethylated melamines and guanamines provide excellent results in a number of aspects, they also have the disadvantage of releasing formaldehyde as a volatile by-product under curing conditions. Because of this, it has long been a desire of industry to find acceptable alternatives which do not emit formaldehyde during cure.

One such alternative which has shown great promise is carbamate and isocyanate functional 1,3,5-triazines, which are disclosed in one or more of commonly owned U.S. Pat. No. 4,939,213, U.S. Pat. No. 5,084,541, U.S. Pat. No. 5,288,865, U.S. application Ser. No. 07/998,313 (filed Dec. 29, 1992), U.S. application Ser. No. 08/061,905 (filed May 14, 1993), U.S. application Ser. No.08/138,581 (filed Oct. 15, 1993) and U.S. application Ser. No. 08/239,009 (filed May 6, 1994), all of which are hereby incorporated by reference herein for all purposes as if fully set forth. Specifically, the carbamate and isocyanate functional 1,3,5-triazines disclosed in these references have been found to be particularly useful as crosslinkers in coating compositions based upon hydroxy functional resins, with the cured coatings possessing a wide range of desirable properties.

The ability of the carbamate and isocyanate functional 1,3,5-triazines to perform as efficient non-formaldehyde emitting crosslinking agents, particularly in curable coating compositions, has initiated intensive research directed towards the discovery of practical and economical processes for their production, a number of which are disclosed in the previously incorporated references. While a number of these processes have shown great promise, certain of them also have some drawbacks including, for example, the required use of exotic and/or expensive starting materials.

In addition to the processes of the aforementioned references, it now been surprisingly discovered that carbamate and isocyanate functional 1,3,5-triazines can also be prepared by carboxylation of amino-1,3,5-triazines in the presence of a base to initially produce a carboxylated amino-1,3,5-triazine intermediate, followed by further reaction thereof with (i) a hydrocarbylating agent to produce the desired carbamate functional 1,3,5-triazine, or (ii) a dehydrating agent to produce the desired isocyanate functional 1,3,5-triazine.

It should be noted that it is generically known to react amines with carbon dioxide under a variety of conditions to form carboxylated derivatives of such amines. See, for example, U.S. Pat. Nos. 4,102,801, 4,192,815, 4,400,526, 4,467,089, 5,055,577, 5,189,205, 5,200,547 and 5,223,638; European Patent Application Publication Nos. 0511948 and 0556538; International Application Publication Nos. WO94/08951, WO94/08952 and WO94/08953; Yoshida and Inoue, "A New Synthesis of Carbamic Esters from Carbon Dioxide, Epoxies, and Amines," *J. Chem. Soc. Perkin I*, 3146–50 (1979); Tsuda et al, "Preparation of Urethanes from Carbon Dioxide via a Copper(I) Carbamato Complex," *J.C.S. Chem. Comm.*, 815–16 (1978); Yoshida et al, "A Direct Synthesis of Carbamate Ester from Carbon Dioxide, Amine and Alkyl Halide," *Chemistry Letters*, 1571–72 (1984); Yoshida et al, "Novel Synthesis of Arylcarbamaic Esters from Carbon Dioxide and Aromatic Amine via a Zinc Carbamate," *Bull. Chem. Soc. Jpn.*, 61, 2913–16 (1988); Yoshida et al, "Novel Synthesis of Carbamate Esters from Carbon Dioxide, and Amines, and Alkyl Halides," *Bull. Chem. Soc. Jpn.*, 62, 1534–38 (1989); Yamazaki et al, "Polycarbonate, -Urethane and -Urea from Carbon Dioxide and Carbonates," Polymer Preprints, National ACS Meeting, 146–49 (Honolulu, Hi. 1979); Arresta and Quaranta, "Role of the Macrocyclic Polyether in the Synthesis of N-alkylcarbamate Esters from Primary Amines, $CO_2$ and Alkyl Halides in the Presence of Crown-Ethers," *Tetrahedron*, 48(8), 1515–30 (1992); and McGhee et al, "Highly Selective Generation of Urethanes from Amines, Carbon Dioxide and Alkyl Chlorides," *J. Chem. Soc., Chem. Commun.*, 699–700 (1994). None of these references, however, disclose or even suggest that such reactions are applicable to amino-1,3,5-triazines.

Indeed, it is well known to those of ordinary skill in the art that the amine functionality of amino-1,3,5-triazines, such as the amino groups of melamines and guanamines, is not equivalent to other types of typical amine functionality. Significantly, melamines and guanamines are among the least reactive of the "amines" and the most difficult to functionalize, and their behavior cannot normally be correlated to that of other known amines, even structurally similar amines such as pyrimidines.

For example, most "typical" amines are highly reactive with acid halides. In a publication by E. M. Smolin and L. Rappaport entitled "S-Triazines and Derivatives," Interscience Publishers Inc., New York, page 333 (1959), it is reported that attempts to react an acid halide with the amino group on a 1,3,5-triazine such as melamine were not successful. Further, attempts to functionalize amino-1,3,5-triazines often results in substitution at the nitrogen on the triazine ring. For example, it is known that the reaction of melamine with alkyl halides, such as allyl chloride, results in alkyl substitution at the nitrogen on the triazine ring resulting in isomelamine derivatives.

It is, therefore, clearly surprising in light of the state of the art that amino-1,3,5-triazines can be carboxylated and further derivatized to produce the desired carbamate and isocyanate functional derivatives via the present inventive process, as described in further detail below.

SUMMARY OF THE INVENTION

As indicated above, the present invention includes a process for preparing a carboxylated amino-1,3,5-triazine comprising, in its overall concept, the step of contacting:

(i) an amino-1,3,5-triazine having at least one $NH_2$ group,
(ii) carbon dioxide and
(iii) a base, under reaction conditions sufficient to produce a corresponding carboxylated amino-1,3,5-triazine. Also included in the present invention is the carboxylated amino-1,3,5-triazine obtainable by this process.

Still further included in the present invention is (i) a process for preparing carbamate functional 1,3,5-triazines by contacting such carboxylated amino-1,3,5-triazines and a hydrocarbylating agent under reaction conditions sufficient to produce a carbamate functional 1,3,5-triazine, and (ii) a process for preparing isocyanate functional 1,3,5-triazines by contacting such carboxylated amino-1,3,5-triazines and a dehydrating agent under reaction conditions sufficient to produce an isocyanate functional 1,3,5-triazine.

The so-produced carbamate and isocyanate functional 1,3,5-triazines, when they contain on average at least two carbamate or isocyanate groups per molecule, are particularly suitable as crosslinking agents as set forth in a number of the previously incorporated references.

The advantages of the present invention include (1) using readily available starting materials such as amino-1,3,5-triazines, (2) using non-toxic carbon dioxide as the carbonyl source, and (3) avoiding the use of environmentally undesirable formaldehyde in the production of crosslinking agents.

These and other features and advantages will become more readily available to those of ordinary skill in the art from a reading of the following detailed description.

DETAILED DESCRIPTION OF THE PREFERRED EMBODIMENTS

As indicated above, the present invention includes a process for carboxylating amino-1,3,5-triazines to produce carboxylated amino-1,3,5-triazines, which can be further derivatized, for example, with a hydrocarbylating agent to produce a corresponding carbamate functional derivative, or with a dehydrating agent to produce a corresponding isocyanate functional derivative.

The term "amino-1,3,5-triazine," in the context of the present invention, refers to 1,3,5-triazine compounds containing at least one unsubstituted amino group ($-NH_2$) as a substituent attached to the 1,3,5-triazine core.

The term "carboxylation," in the context of the present invention, refers to a chemical reaction by which a carboxyl ($-COOH$) group or a carboxylate salt group ($-COO^{-+}$ cation) is introduced into at least a portion of the amino groups of the 1,3,5-triazine starting material. Without being bound by theory, it is believed that carboxylation takes place only at the sites of the amino groups of the 1,3,5-triazines. The actual mechanism of carboxylation of such amino-1,3, 5-triazines, however, is unclear.

In view of the meaning of carboxylation, a "carboxylated" product, in the context of the present invention, refers to a 1,3,5-triazine product with a substituent containing an aminocarboxyl ($-NH-COOH$) group or the salt thereof ($-NH-COO^{-+}$cation) which is the result of the carboxylation of an amino group of the amino-1,3,5-triazine. For example, the fully carboxylated product of melamine (2,4, 6-triscarboxylamino-1,3,5-triazine) is a carboxylated product in the context of the present invention.

A "carbamate functional" 1,3,5-triazine, in the context of the present invention, refers to 1,3,5-triazine compounds containing at least one carbamate group ($-NH-COOR$, R=hydrocarbyl) as a substituent attached to the 1,3,5-triazine core. An "isocyanate functional" 1,3,5-triazine, in the context of the present invention, refers to 1,3,5-triazine compounds containing at least one isocyanate group ($-N=C=O$) as a substituent attached to the 1,3,5-triazine core.

The Amino-1,3,5-Triazine Starting Material

As preferred amino-1,3,5-triazines for use in the process of the present invention may be mentioned compounds represented by the formula:

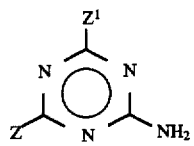

wherein

Z and $Z^1$ are independently selected from the group consisting of hydrogen, a hydrocarbyl, a hydrocarbyloxy, a group represented by the formula $-N(Q)_2$, and a group represented by the formula:

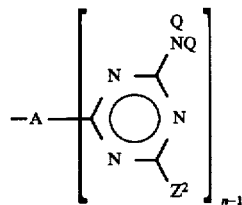

A is an n-functional anchor, n is at least 2, each Q is independently selected from the group consisting of hydrogen and a hydrocarbyl, and each $Z^2$ is independently selected from the group consisting of hydrogen, a hydrocarbyl, a hydrocarbyloxy and a group represented by the formula $-N(Q)_2$.

The term "hydrocarbyl," in the context of the present invention, is a group which contains carbon and hydrogen atoms and includes, for example, alkyl, aryl, aralkyl, alkenyl, and substituted derivatives thereof. Likewise, the term "hydrocarbylene" (as utilized below) refers to a divalent hydrocarbyl such as, for example, alkylene, arylene, aralkylene, alkenylene, and substituted derivatives thereof.

The group A in the above formula is an n-functional anchor which can, for example, be a hydrocarbon residue (e.g., a hydrocarbylene group such as a methylene group), an amino compound residue, NH, N(hydrocarbyl), O, S, $CO_2$, $NHCO_2$, $CO(NH)_2$ and the like. Amino-1,3,5-triazines containing this group A are referred to herein as oligomeric amino-1,3,5-triazines. As specific illustrative examples of oligomeric amino-1,3,5-triazines may be mentioned, for example, the self-condensation product of a melamine-formaldehyde resin, or the oligomer produced by the condensation of n moles of a melamine-formaldehyde resin with one mole of a n-functional polyol, such a trimethylolpropane.

Most preferred for use in the present invention are such amino-1,3,5-triazines having at least two $-NH_2$ groups, and particularly the substantially monomeric amino-1,3,5-triazines (i) wherein both Z and $Z^1$ are represented by the formula $-N(Q)_2$ (melamines), and (ii) wherein $Z^1$ is hydrogen or a hydrocarbyl, and Z is represented by the formula $-N(Q)_2$ (guanamines).

The preferred melamines are those wherein each Q is hydrogen, that is, melamine.

The preferred guanamines are those represented by the above general formula wherein $Z^1$ is more preferably selected from the group consisting of an alkyl of 1 to 20 carbon atoms, alkenyl of 3 to 20 carbon atoms, aryl of 6 to 20 carbon atoms, and aralkyl of 7 to 20 carbon atoms; and Z is —N(Q)$_2$ with each Q being hydrogen. As specific preferred examples may be mentioned acetoguanamine, ethylcarboguanamine, cyclohexylcarboguanamine and benzoguanamine.

Carbon Dioxide

The carbon dioxide which can be employed in the present invention may be pure carbon dioxide or may contain inert gases such as, for example, nitrogen, argon and/or helium. Generally, any commercially available carbon dioxide may be utilized.

The Base

The base used in the present invention is preferably one of a sufficient strength to "deprotonate" an amino group of the amino-1,3,5-triazine. By "deprotonation" is it meant an actual deprotonation of such amino group (generation of an —NH$^-$) or an effective deprotonation whereby the proton is ultimately removed via a coordination reaction involving the base. Thus, based upon the choice of the amino-1,3,5-triazine, one of ordinary skill in the art will readily be able to determine, with at most only minor experimentation, which specific bases "deprotonate" an amino group in the amino-1,3,5-triazine and are, consequently, suitable for use in the present invention.

As suitable bases may be mentioned strong bases comprising metals such as alkali, alkaline earth and copper, cations such as phosphonium and ammonium, and counter-anions such as alkoxide, hydride, oxide, hydroxide, carbonate, in addition to nitrogenous bases such as tertiary amines. As preferred examples of suitable bases may be mentioned alkali metal hydrides, alkali metal oxides, alkali metal carbonates, aliphatic and aromatic tertiary amines, and mixtures thereof. Sodium and potassium hydrides and tertiary amines are most preferred, including triethylamine, N-methyl diisopropylamine, tri-n-butylamine, tri-n-octylamine, 1,4-diaza-bicyclo-(2.2.2)-octane(DABCO), 1,5-diaza-bicyclo-(4.3.0)-non-5-ene(DBN) and 1,8-diazabicyclo-(5.4.0)-undec-7-ene(DBU), as well as mixtures thereof.

The Hydrocarbylating Agent

The hydrocarbylating agents suitable for use in the production of carbamate functional 1,3,5-triazines from the carboxylated amino-1,3,5-triazines in accordance with the present invention have the general formula:

R—(X)$_n$ wherein R is a hydrocarbyl group, X is a leaving group and n is greater than or equal to 1.

The hydrocarbyl group R is preferably selected from the group consisting of a linear, branched, or cyclic alkyl of 1 to 20 carbon atoms; an alkenyl of 3 to 20 carbon atoms; an aralkyl of 7 to 20 carbon atoms; and alkylene oxides.

The leaving group X is preferably selected from the group consisting of a halogen such as chloride, bromide or iodide; an alkanesulfonate; an arenesulfonate; a perfluoroalkane sulfonate; a perfluoroarenesulfonate; and an alkyl sulfate.

Especially preferred hydrocarbylating agents include, for example, alkyl halides of 1 to 4 carbon atoms.

It should be noted that multifunctional hydrocarbylating agents may also be utilized for producing oligomeric carbamate functional 1,3,5-triazines.

The Dehydrating Agent

The dehydrating agents suitable for use in the production of carbamate functional 1,3,5-triazines from the carboxylated amino-1,3,5-triazines in accordance with the present invention include those mentioned in previously incorporated WO94/08951, WO94/08953, U.S. Pat. No. 4,192,815 and U.S. Pat. No. 5,189,205.

Such dehydrating agents include electrophilic and oxophilic dehydrating agents such as, for example, PO(hal)$_3$, P(hal)$_3$, SO(hal)$_2$, SO$_2$(hal)$_2$, S(hal)$_2$, SO$_3$, P(hal)$_5$, P$_2$O$_5$, NO, NO$_2$, NO(hal), ketene, acid anhydrides, acid halides, and halides and oxyhalides of various metals.

Process Conditions

In the practice of the invention, the amino-1,3,5-triazine, carbon dioxide and a base are contacted under reaction conditions (such as temperature, pressure and time) sufficient to produce a corresponding carboxylated amino-1,3,5-triazine. Preferably, the amino-1,3,5-triazine and a base are contacted in a first step, followed by the introduction of carbon dioxide into the reaction zone under atmospheric or superatmospheric pressures, at a temperature in the range of from about 25° C. to about 90° C., and for a period typically in the range of from about 1 to about 24 hours, to produce a corresponding carboxylated amino-1,3,5-triazine.

The amounts of the various ingredients useable in the process of the invention depends on the number of —NH$_2$ groups present in the amino-1,3,5-triazine. In theory, one equivalent of carbon dioxide per —NH$_2$ group is required to completely carboxylate the same; however, a substantial excess is preferably utilized. The amount of base required for the reaction can vary widely, but preferably at least one equivalent, and more preferably greater than one equivalent, is used to ensure higher conversion.

The carboxylated amino-1,3,5-triazine resulting from the procedure described above may be represented by the following general formula:

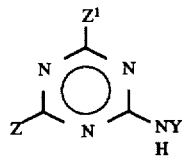

wherein

Z and Z$^1$ are independently selected from the group consisting of hydrogen, a hydrocarbyl, a hydrocarbyloxy, a group represented by the formula —N(Q)$_2$, and a group represented by the formula:

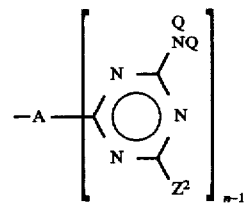

A is an n-functional anchor, n is at least 2, each Z$^2$ is independently selected from the group consisting of hydrogen, a hydrocarbyl, a hydrocarbyloxy and a group represented by the formula —N(Q)$_2$, each Q is independently selected from the group consisting of hydrogen, a hydrocarbyl and a group Y, with the proviso that no more than one Q in each —N(Q)$_2$ is Y, and Y is selected from the group consisting of a carboxyl group and a carboxylate salt group.

The corresponding carboxylated derivatives of preferred amino-1,3,5-triazines described above are those wherein:

(i) both Z and Z$^1$ are represented by the formula —N(Q)$_2$ (carboxylated melamines), and particularly those which contain at least two groups Y and especially three groups Y; and (ii) wherein $Z^1$ is hydrogen or a hydrocarbyl (more preferably as specifically described above), and Z is represented by the formula —N(Q)$_2$ (carboxylated guanamines), and particularly those which contain two groups Y.

When the group Y is the carboxylate salt group, the cation therefore will be generated from the base or bases utilized in the production process. As examples of such cations may be mentioned alkali metal cations such as sodium, potassium and cesium; phosphonium ions; and ammonium ions.

The carboxylated amino-1,3,5-triazine as described above may then be converted to a corresponding carbamate functional 1,3,5-triazine by contact with a hydrocarbylating agent under reaction conditions (such as temperature and time) sufficient to produce such corresponding carbamate functional 1,3,5-triazine. Preferably, the reactants are contacted at a temperature in the range of from about 25° C. to about 80° C., and for a period typically in the range of from about 1 to about 24 hours, to produce the desired carbamate functional 1,3,5-triazines. Although not specifically required, it is preferred that the reaction is carried out under an atmosphere of $CO_2$. To fully convert the carboxyl/ carboxylate salt groups to carbamate groups, at least one equivalent of hydrocarbylating agent, and preferably an equivalent excess, should be utilized per carboxyl/ carboxylate salt equivalent.

The carboxylated amino-1,3,5-triazine as described above may then be converted to a corresponding isocyanate functional 1,3,5-triazine by contact with a dehydrating agent under reaction conditions (such as temperature and time) sufficient to produce such corresponding isocyanate functional 1,3,5-triazine. Preferably, the reactants are contacted at a temperature in the range of from about −78° C. to about 100° C., and for a period typically in the range of from about 1 to about 24 hours, to produce the desired isocyanate functional 1,3,5-triazines. Although not specifically required, it is preferred that the reaction is carried out under an atmosphere of $CO_2$. To fully convert the carboxyl/ carboxylate salt groups to isocyanate groups, at least one equivalent of dehydrating agent, and preferably an equivalent excess, should be utilized per carboxyl/carboxylate salt equivalent.

In both the carboxylation and subsequent derivation reactions, the reactants are preferably contacted in the presence of a reaction medium in which one or more reactants and/or the base are suspended or dissolved. The reaction medium typically is a solvent for at least one of the components, and typically the amino-1,3,5-triazine. The preferred solvents which are substantially inert with the reactants under the conditions described above and include, for example, N,N-dimethylformamide (DMF), glyme, diglyme, and higher glycol ethers, dioxane, dimethyl sulfoxide, N,N-dimethylacetamide, N-methylpyrrolidone, and the like.

As indicated above, the at least bis-carbamate and bis-isocyanate functional 1,3,5-triazines have known utility as crosslinking agents for hydroxy functional resins in curable compositions containing them, usable in a variety of applications including coatings, adhesives and molding.

The following examples further illustrate the present invention. They are not to be construed as limiting the claims in any manner.

EXAMPLE 1

To an oven-dried 50 ml round-bottomed flask was added 500 mg (4 mmol) of melamine, 10 ml of anhydrous dimethylformamide (DMF), and 360 mg (15 mmol) of sodium hydride. The resulting slurry was stirred at room temperature for 30 minutes. Carbon dioxide gas was then bubbled through the reaction slurry on a continuous basis throughout the preparation. The mixture was then heated to 75° C. and held for 1.5 hours. Upon cooling, n-butyl bromide (2.74 g, 20 mmol) was added and the mixture was allowed to stir at room temperature for another two hours. The reaction temperature was then adjusted to approximately 70° C. and held for 16 hours. The bubbling of carbon dioxide was stopped at this point. Upon cooling, the resulting mixture was filtered to remove salts and unreacted melamine. The filtrate was then concentrated under reduced pressure, resulting in 530 mg of a brownish-yellow product which, by mass spectroanalysis using Fast Atom Bombardment techniques (FAB), was determined to contain both 2,4,6-tris (butoxycarbonylamino)-1,3,5-triazine and 2,4-bis (butoxycarbonylamino)-6-amino-1,3,5-triazine.

EXAMPLE 2

To an oven-dried 50 ml round-bottom flask was added 0.50 g(4 mmol) of melamine, 10 ml of anhydrous DMF, and 3.65 g (24 mmol) of 1,8-diazabicyclo-(5.4.0)-undec-7-ene (DBU). Carbon dioxide gas was then bubbled through the reaction slurry on a continuous basis throughout the preparation. The mixture was then heated to 50° C. and held for one hour, then cooled to room temperature and stirred for another 1.5 hours. n-Butyl bromide (3.8 g, 20 mmol) was added and the mixture was then heated to approximately 75°–80° C. under carbon dioxide for 5 hours. Upon cooling, the resulting mixture was stirred at room temperature for another 14 hours. The bubbling of carbon dioxide was stopped at this point. Filtration followed by concentration of the filtrate under reduced pressure resulting in 0.20 g of a yellow oily product which, by mass spectroanalysis using FAB, was determined to contain 2,4-bis (butoxycarbonylamino)-6-amino-1,3,5-triazine.

EXAMPLE 3

To an oven-dried 50 ml round-bottomed flask was added 4 ml of anhydrous DMF and 310 mg (13 mmol) of sodium hydride. To the resulting slurry was then added dropwise a solution of benzoguanamine (1.12 g, 6 mmol) in 10 ml of anhydrous DMF. The reaction temperature rose from 24° to 32° C. during the course of the addition. The resulting brownish slurry was then heated to 57° C. with stirring under nitrogen for 30 minutes. After cooling to 35° C., dried carbon dioxide gas was bubbled through the reaction slurry on a continuous basis throughout the preparation. The reaction mixture immediately became a thick paste upon $CO_2$ addition and reaction temperature rose to approximately 48° C. before cooling back down to room temperature. Additional dried DMF (5 ml) was added to facilitate stirring. At 1.5 hours reaction time, n-butyl bromide (2.55 g, 18.6 mmol) and Aliquat® 336 (tricaprylmethylammonium chloride) (0.15 g, 0.4 mmol) were added and the mixture was heated to 53° C. under a flow of carbon dioxide for three hours and then the mixture was heated at 70° C. for an additional 17 hours. The bubbling of carbon dioxide was stopped at this point. Upon cooling, 25 ml of dichloromethane was added to the reaction followed by filtration. The resulting filtrate was then poured into an amount of 0.05N aqueous sulfuric acid solution sufficient to provide a pH in the range of 6–7 in the aqueous layer. Additional dichloromethane was then added, the organic layer separated, and washed with deionized water. Drying of the organic layer, concentrating under reduced pressure, and triturating with methanol resulted in 0.18 g of a white solid.

$^1$H-NMR and mass spectroanalysis using FAB showed that the isolated product contained both 2,4-bis (butoxycarbonylamino)-6-phenyl-1,3,5-triazine and 2-(butoxycarbonylamino)-4-amino-6-phenyl-1,3,5-triazine.

EXAMPLE 4

In a glass lined Parr reactor, a slurry of benzoguanamine (1.12 g) and sodium hydride (0.33 g) in anhydrous DMF (50 ml) under nitrogen was heated at 40° C. for 30 minutes. After cooling, carbon dioxide was introduced under pressure (100 psig). An exothermic reaction raised the temperature to about 40° C. After 2 hours at 46° C., n-butyl bromide (2.55 g) was added through a high pressure syringe pump over a period of 3 minutes. After 20 hours at 72° C., the mixture was cooled, the pressure released, dichloromethane (50 ml) added, and the product filtered. The filtrate was poured into water containing sufficient dilute sulfuric acid to produce a pH of 6-7. The organic layer was washed with deionized water. Drying and removing the solvent resulted in 0.31 g of a yellow gummy solid which, after analysis by $^1$H-NMR and mass spectroanalysis using FAB, was determined to contain both 2,4-bis-(butoxycarbonylamino)-6-phenyl-1,3,5-triazine and 2-(butoxycarbonylamino)-4-amino-6-phenyl-1,3,5-triazine.

EXAMPLE 5

A slurry of benzoguanamine (1.12 g) and cesium carbonate (4.89 g) in anhydrous DMF (20 ml) under nitrogen was heated at 80° C. for 60 minutes. The reaction mixture was then cooled to room temperature and, after 1.5 hours at room temperature, carbon dioxide was introduced continuously under atmospheric pressure. After an additional 0.5 hours at room temperature, n-butyl bromide (2.55 g) was added and the mixture was heated to 55° C. for 18 hours. Carbon dioxide flow into the system was maintained throughout this period. The mixture was then cooled and, after adding dichloromethane (25 ml), was filtered. The filtrate was poured into water containing sufficient dilute sulfuric acid to produce a pH of 4.5. The organic layer was separated, washed with deionized water and dried to remove residual solvent, resulting in 0.46 g of a yellow gummy solid which, by $^1$H-NMR and mass spectroanalysis using FAB, was determined to contain 2-(butoxycarbonylamino)-4-butylamino-6-phenyl-1,3,5-triazine.

EXAMPLE 6

A slurry of benzoguanamine (1.12 g) and sodium hydride (0.35 g) in anhydrous N-methylpyrrolidone (20 ml) under nitrogen was stirred at 25° C. for 30 minutes. While at room temperature, dried carbon dioxide was introduced continuously under atmospheric pressure to give a thick, mustard colored paste and raising the temperature of the mixture to 45° C. After cooling and an additional 1.5 hours at room temperature, n-butyl bromide (2.55 g) was added and the mixture was stirred at room temperature under a flow of carbon dioxide for 4 hours, followed by heating at 47° C. for an additional 18 hours. Carbon dioxide was continuously introduced into the system throughout this period. The mixture was then cooled and, after adding dichloromethane (25 ml), was filtered. The filtrate was poured into water containing sufficient dilute sulfuric acid to produce a pH of 6-7. The organic layer was separated, washed with deionized water, and dried to remove any solvent, resulting in 0.16 g of a yellow gummy solid which, by $^1$H-NMR and mass spectroanalysis using FAB, was determined to contain 2-(butoxycarbonylamino)-4-butylamino-6-phenyl-1,3,5-triazine.

EXAMPLE 7

A slurry of melamine (0.5 g) and potassium tertiary butoxide (1.79 g) in anhydrous dimethyl sulfoxide (20 ml) under nitrogen was stirred at 45° C. for 45 minutes. Upon cooling to room temperature, carbon dioxide was introduced continuously under atmospheric pressure raising the temperature of the mixture to about 56° C. After cooling and 2 hours at room temperature, n-butyl iodide (3.31 g) was added through a syringe and the mixture was stirred at room temperature under a flow of carbon dioxide for 19 hours. Then, the mixture was heated at 55° C. for an additional 1 hour. Carbon dioxide was continuously introduced into the system throughout the reaction. After cooling to room temperature, the carbon dioxide addition was discontinued, and after adding dichloromethane (25 ml), the mixture was filtered. The filtrate was poured into water containing sufficient dilute sulfuric acid to produce a pH of 7. The organic layer was separated, washed once with water, and dried (sodium sulfate), resulting in 0.02 g of a yellow gummy solid which, by analysis with $^1$H-NMR and mass spectroanalysis using FAB, was determined to contain 2,4,6-tris (butoxycarbonylamino)-1,3,5-triazine,2-(butoxycarbonylamino)-4,6-diamino-1,3,5-triazine, and 2-(butoxycarbonylamino)-4-butylamino-6-amino-1,3,5-triazine.

Although the present invention is described with reference to certain preferred embodiments, it is apparent that modifications and variations thereof may be made by those skilled in the art without departing from the scope of this invention as defined by the appended claims.

We claim:

1. A process for preparing a carbamate functional 1,3,5-triazine comprising the steps of:
   A. contacting
      (i) an amino-1,3,5-triazine of the general formula

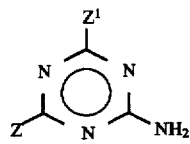

wherein
   Z and $Z^1$ are independently selected from the group consisting of hydrogen, a hydrocarbyl, a hydrocarbyloxy and a group represented by the formula $—N(Q)_2$,
   (ii) carbon dioxide and
   (iii) a base,
   under reaction conditions sufficient to produce a carboxylated amino-1,3,5-triazine; and
   B. contacting the carboxylated amino-1,3,5-triazine and a hydrocarbylating agent under reaction conditions sufficient to produce a carbamate functional 1,3,5-triazine.

2. The process of claim 1, wherein Z is $—N(Q)_2$; $Z^1$ is selected from the group consisting of hydrogen, a hydrocarbyl, a hydrocarbyloxy and a group of the formula $—N(Q)_2$; the base is of sufficient strength to deprotonate an amino group of the amino-1,3,5-triazine; at least one equivalent of carbon dioxide is utilized per $—NH_2$ equivalent of the amino-1,3,5-triazine; the carbon dioxide is introduced under superatmospheric pressure; the reaction is conducted in the presence of a reaction medium; and the hydrocarbylating agent has the general formula R—(X)$_n$ wherein R is a hydrocarbyl group, X is a leaving group and n is.

3. The process of claim 2, wherein Z is —N(Q)$_2$.

4. The process of claim 3, wherein $Z^1$ is group selected from the group consisting of hydrogen, a hydrocarbyl, a hydrocarbyloxy and a group of the formula —N(Q)$_2$.

5. The process of claim 4, wherein $Z^1$ is a hydrocarbyl selected from the group consisting of a linear, branched, or cyclic alkyl of 1 to 20 carbon atoms, an alkenyl of 3 to 20 carbon atoms, an aryl of 6 to 20 carbon atoms, and an aralkyl of 7 to 20 carbon atoms.

6. The process of claim 5, wherein all Q groups are hydrogen.

7. The process of claim 4, wherein $Z^1$ is —N(Q)$_2$.

8. The process of claim 7, wherein all Q groups are hydrogen.

9. The process of claim 1, wherein the base is of sufficient strength to deprotonate an amino group of the amino-1,3,5-triazine.

10. The process of claim 1, wherein the base is selected from the group consisting of metal alkoxides, metal hydrides, metal oxides, metal hydroxides, metal carbonates, phosphoniums, ammoniums, tertiary amines and mixtures thereof.

11. The process of claim 10, wherein the base is selected from the group consisting of alkali metal hydrides, alkali metal oxides, alkali metal carbonates, aliphatic tertiary amines, aromatic tertiary amines, and mixtures thereof.

12. The process of claim 1, wherein at least one equivalent is base is utilized per —NH$_2$ equivalent of the amino-1,3,5-triazine.

13. The process of claim 1, wherein at least one equivalent of carbon dioxide is utilized per —NH$_2$ equivalent of the amino-1,3,5-triazine.

14. The process of claim 1, wherein the carbon dioxide is introduced under superatmospheric pressure.

15. The process of claim 1, wherein the reactants are contacted at a temperature in the range of from about 25° C. to about 90° C.

16. The process of claim 1, wherein the reactants are contacted for a period of from about 1 hour to about 24 hours.

17. The process of claim 1, wherein the reaction is conducted in the presence of a reaction medium.

18. The process of claim 1, wherein the hydrocarbylating agent has the general formula:

R—(X)$_n$ wherein

R is a hydrocarbyl group, X is a leaving group and n is 1.

19. The process of claim 18, wherein R is selected from the group consisting of a linear, branched, or cyclic alkyl of 1 to 20 carbon atoms; an alkenyl of 3 to 20 carbon atoms; an aralkyl of 7 to 20 carbon atoms; and alkylene oxides.

20. The process of claim 18, wherein X is selected from the group consisting of a halogen; an alkanesulfonate; an arenesulfonate; a perfluoroalkane sulfonate; a perfluoroarenesulfonate; and an alkyl sulfate.

21. The process of claim 18, wherein the hydrocarbylating agent is an alkyl halide of 1 to 4 carbon atoms.

22. The process of claim 2, wherein all Q groups are hydrogen.

23. The process of claim 22, wherein $Z^1$ is —N(Q)$_2$.

* * * * *

UNITED STATES PATENT AND TRADEMARK OFFICE
CERTIFICATE OF CORRECTION

PATENT NO. : 5,792,865
DATED : August 11, 1998
INVENTOR(S) : Lawrence Allen Flood and Ram Baboo Gupta It is certified that error appears in the above-identified patent and that said Letters Patent is hereby corrected as shown below:

Column 11, line 7, claim 2
"n is." should read --n is 1.--

Column 11, line 8, claim 3
"The process of claim 2" should read --The process of claim 1--

Signed and Sealed this

Twenty-second Day of December, 1998

*Attest:*

BRUCE LEHMAN

*Attesting Officer*     *Commissioner of Patents and Trademarks*